United States Patent
Martinelli et al.

(10) Patent No.: US 8,440,985 B2
(45) Date of Patent: May 14, 2013

(54) METHOD AND A DEVICE FOR DETECTING THE FLUORESCENCE OF A BIOCHIP

(75) Inventors: Lucio Martinelli, Paris (FR); Yann Marcy, Paris (FR); Henri Benisty, Palaiseau (FR)

(73) Assignee: Genewave, Evry (FR)

( * ) Notice: Subject to any disclaimer, the term of this patent is extended or adjusted under 35 U.S.C. 154(b) by 0 days.

(21) Appl. No.: 13/000,549

(22) PCT Filed: Jun. 23, 2009

(86) PCT No.: PCT/FR2009/000757
§ 371 (c)(1),
(2), (4) Date: Mar. 25, 2011

(87) PCT Pub. No.: WO2010/007233
PCT Pub. Date: Jan. 21, 2010

(65) Prior Publication Data
US 2011/0266460 A1    Nov. 3, 2011

(30) Foreign Application Priority Data
Jun. 24, 2008    (FR) .................................... 08 03528

(51) Int. Cl.
*G01N 21/64*    (2006.01)

(52) U.S. Cl.
USPC ...................................................... 250/459.1

(58) Field of Classification Search ................ 250/459.1
See application file for complete search history.

(56) References Cited

U.S. PATENT DOCUMENTS

| | | |
|---|---|---|
| 6,479,301 B1 | 11/2002 | Balch et al. |
| 6,608,918 B1 | 8/2003 | Rushbrooke et al. |
| 7,160,687 B1 | 1/2007 | Kapur et al. |
| 2002/0097899 A1 | 7/2002 | Kimura et al. |
| 2003/0157581 A1 | 8/2003 | Grill et al. |
| 2003/0157586 A1 | 8/2003 | Bonde et al. |
| 2004/0132128 A1 | 7/2004 | Shvets et al. |
| 2005/0201899 A1* | 9/2005 | Weisbuch .................. 422/82.11 |

OTHER PUBLICATIONS

International Search Report and Written Opinion for PCT/FR2009/000757 dated Nov. 17, 2009.

\* cited by examiner

*Primary Examiner* — Kiho Kim
(74) *Attorney, Agent, or Firm* — Alston & Bird LLP

(57) ABSTRACT

An imaging method and a device for detecting the fluorescence of a biochip by illuminating chromophores associated with probes (14) of a substrate (12) placed on a sensor (10) having photodetectors, e.g. of the CCD or CMOS type, a stop filter that rejects the excitation light of the chromophores being provided between the probes (14) and the sensor, the substrate (12) being separable from the sensor (10) after use so as to enable the sensor to be reused.

13 Claims, 1 Drawing Sheet

METHOD AND A DEVICE FOR DETECTING THE FLUORESCENCE OF A BIOCHIP

FIELD OF THE INVENTION

The invention relates to a method and to a device for detecting the fluorescence of a biochip, and more particularly for imaging and detecting the fluorescence emitted by chromophores fixed on a substrate of the biochip.

BACKGROUND OF THE INVENTION

Biochips are nowadays in widespread use both in research and in industry. Essentially they comprise a generally flat solid substrate on which biomolecules are fixed, such as strands of DNA or RNA, proteins, antigens, antibodies, aptamers, etc. . . . , or indeed entire or fractioned microorganisms such as bacteria, cells, viruses, spores, etc. . . . , or indeed microobjects that themselves carry biomolecules.

Known fluorescence biochips are generally constituted by a glass slide having its surface chemically functionalized, such that after reacting with components of interest, it carries fluorescent spots that respond to light excitation at a given wavelength by emitting light at another wavelength.

The emitted light may be collected by an appropriate optical system and transmitted to a sensor, e.g. using photodetectors of the charge-coupled device (CCD) type or of the complementary metal oxide semiconductor (CMOS) type. The image that is obtained of the surface of the biochip comprises light spots of intensities that are a function of the quantity of chromophores that are present at said spots. In order to analyze these spots appropriately, it is necessary to have an image of the spots that presents sufficient fidelity and resolution.

The chromophores that are placed at the interface between a medium of higher index and a medium of lower index (typically a glass-air or glass-liquid interface) emits preferentially into the higher index medium at a ratio that is equal (to a first approximation) to the cube of the ratio of the refractive indices of the two media, i.e. about 4.1 for glass and air, which means that when the sensor is placed above the biochip, about 80% of the light emission from the chromophores is lost in the glass slide.

In addition, the optical systems used present a numerical aperture that is limited such that only a small fraction of the light emitted into the air can be transmitted to the sensor. The overall efficiency with which the light emitted by the chromophores is collected is then restricted to a few percent.

In order to reduce those drawbacks, proposals have already been made to capture the light the chromophores emit into the higher-index medium. In this context, the simplest implementation consists in using the sensor itself as the substrate of the biochip, and thus in placing an array of biological probes on the surface of the sensor, which probes are subsequently put into contact with the molecules for analysis.

The drawback of that technique is its cost, since each analysis requires a new sensor to be used.

SUMMARY OF THE INVENTION

An essential object of the present invention is to provide a solution to all of the above problems that is simple, inexpensive, and effective.

To this end, the invention provides a method of imaging and detecting the fluorescence emitted by chromophores fixed on a substrate of a biochip, detection consisting in illuminating the chromophores at an excitation wavelength and in picking up the light emitted by the chromophores in response to said illumination, the method being characterized in that it consists in using a substrate that is at least partially transparent at the emission wavelength of the chromophores, the substrate carrying biological probes that are put into contact with looked-for biological targets, in putting the substrate into contact with a sensor, e.g. a matrix of CCD or CMOS type photodetectors or a photosensitive emulsion, while interposing a stop filter between the chromophores and the sensor to reject the excitation wavelength, the filter being transparent at the emission wavelength, and optionally in providing at least partial index continuity between the substrate and the sensor, and then in illuminating the substrate at the excitation wavelength of the chromophores and in using the sensor to detect the light signals emitted by the chromophores.

After these light signals have been acquired, the sensor can be reused for another analysis: it suffices to separate the substrate from the sensor and to replace it with another substrate.

Light signals may be acquired from the chromophores when "dry" in the traditional way, the substrate being dried prior to being placed on the sensor.

It is also possible to interpose a set of optical fibers in the form of a flat block or wafer between the substrate and the sensor or between the substrate and the filter.

In a variant of the invention, the method of the invention provides for placing a fluid flow device on the substrate and fastening it thereto, the fluid flow device having channels and/or chambers for introducing or circulating fluids, and in using the device to bring biological targets into contact with the probes fastened on the substrate.

Under such circumstances, the assembly formed by the fluid flow device and the substrate may be placed on the sensor before the biological targets are put into contact with the probes of the substrate.

The acquisition of images by means of the sensor then makes it possible to track in real time interactions between the targets and the probes, e.g. by analyzing the shapes and the intensities of the spots.

The invention also provides a device for imaging and detecting the fluorescence emitted by chromophores fixed on a substrate of a biochip, the imaging and the detection being performed by executing the above-described method, the device being characterized in that it comprises:

a substrate that is at least partially transparent at the emission wavelength of the chromophores;

a stop filter that rejects the excitation wavelength of the chromophores;

means for imaging, detecting, and acquiring the light emitted by the chromophores in response to being excited by light, these means comprising a sensor of the type comprising a matrix of CCD or CMOS photodetectors, for example, or a photosensitive emulsion; and means for putting the substrate into optical contact with the sensor to form an image of the chromophores on the sensor, and enabling the substrate to be separated from the sensor after it has been used.

By way of example, the substrate comprises a thin plate of glass or sapphire, a film of a plastics material such as polydimethylsiloxane (PDMS), Mylar, Zeonex, a polarizing filter, a set of optical fibers, or a set of capillary tubes containing the probes.

In a variant, the substrate may be formed by the stop filter that rejects light at the excitation wavelength.

Advantageously, the stop filter comprises an absorbent filter, or a reflective filter, or a combination of absorbent and reflective filters, in particular as described in prior application WO 2007/04575 in the name of the applicant.

Means may be provided for ensuring index continuity between the substrate and the sensor, said means comprising a thin layer of liquid or of gel of appropriate index or of flexible material (e.g. PDMS) connecting the substrate to the sensor.

According to another characteristic of the invention, a fluid flow device having channels and/or chambers for introducing or circulating fluid is designed to be placed on the substrate to bring biological targets into contact with probes fastened on the substrate, the device being made of glass by etching or of polymer by molding, thermoforming, or assembling films of polymer that include cutouts corresponding to the above-mentioned channels and/or chambers.

BRIEF DESCRIPTION OF THE DRAWINGS

The invention can be better understood and other characteristics, details, and advantages thereof appear more clearly on reading the following description made by way of example and with reference to the accompanying drawing, in which.

DETAILED DESCRIPTION OF THE INVENTION

Figure 1:
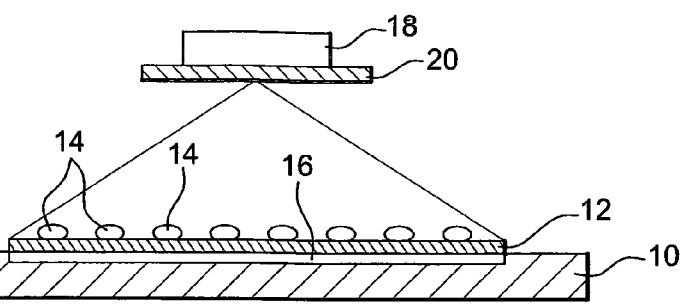
FIG. 1 is a diagram of a detector device of the invention.

Reference is made initially to FIG. 1 which is a diagram of a detector device of the invention, in which detection is performed "dry".

The device comprises a sensor 10, e.g. of the type comprising a matrix of CCD or CMOS photodetectors, or in a variant a medium with a photosensitive emulsion, onto which a thin substrate 12 is placed, the substrate having a series of biological probes 14 arranged on its top surface, e.g. arranged in an array.

These probes are put into contact with biological targets of interest, in conventional manner, which targets become fixed on the corresponding probes, and such fixing is revealed by fluorescent markers. After the targets have been fixed on the probes 14, the substrate 12 is washed, then dried, and subsequently placed on the sensor 10, being positioned on the sensor in such a manner as to ensure that an image is indeed formed of the entire zone for analysis, possibly with a layer of material being interposed, e.g. a layer of a liquid or a gel or a flexible film, serving to provide at least partial index continuity between the substrate 12 and the sensor 10.

The substrate 12 is illuminated by a suitable light source, such as for example a laser or light-emitting diode (LED) generator 18 associated with a filter 20, the source emitting at an excitation wavelength of the fluorescent markers and being placed above the substrate 12, thereby enabling an image of the zone containing the probes 14 to be acquired, which image is analyzed to detect and count the biological targets that have become fixed on the probes 14.

Between the fluorescent markers and the sensor 10, it is necessary to install a stop filter that rejects the light for exciting the fluorescent markers, the filter having a rejection ratio at the excitation wavelength of at least $10^{-5}$ and being transparent at least in a portion of emission spectrum of the fluorescent markers.

The rejection filter may constitute the substrate 12 itself or it may be interposed between the substrate and the sensor 10. It may be constituted by an absorbent filter or by a reflective filter or by a combination thereof, as already described in prior application WO 2007/04575 in the name of the applicant. By way of example, a reflective filter may be placed on the substrate 12 and an absorbent filter may be placed on the sensor 10. This combination makes it possible to benefit from amplification of the light for exciting the fluorescent markers by means of a constructive interference effect, and also from an amplification of the fluorescence emitted by the markers. The filter may also be placed on a flat wafer or block 16 of optical fibers mounted between the substrate and the sensor.

The substrate is at least partially transparent at the wavelengths of the emission spectrum of the above-mentioned chromophores or fluorescent markers. In practice, the ratio of its transmittances at the emission and excitation wavelengths of the chromophores or markers is at least $10^5$.

After acquiring the image provided by the sensor 10, the substrate 12 may be separated therefrom and replaced by another substrate 12 for acquiring a new image.

The substrate may be placed on the sensor in the manner shown in the drawing, being in contact with the sensor via its face opposite to its face carrying the markers. In a variant, it is the face of the substrate carrying the markers that may be put into contact with the sensor.

In the variant embodiment shown in FIGS. 2 to 6, a fluid flow device is associated with the substrate for putting biological targets into contact with the probes carried by the substrate.

The fluid flow device 22 comprises channels and/or chambers for introducing and circulating fluids, the device being made of glass or of polymer, e.g. by molding, by thermoforming, or by assembling films.

In particular, it is possible to cast a curable or polymerizable polymer into a mold, e.g. a polymer of the PDMS type (polydimethylsiloxane), or an optical adhesive (Norland optical adhesive (NOA)), with the bottom of the mold having a structure in relief that corresponds to the channels and/or chambers that are to be obtained. The polymer is subsequently cured or polymerized, at least in part, so that the molding is strong enough to be handled. In a variant, the device 22 may be formed by assembling polymer films, some of which contain cutouts, e.g. made by laser, so as to produce the desired channels and/or chambers.

In another variant, the device 22 is made by thermoforming a polymer material that is pressed against a hot mold.

Figure 2:
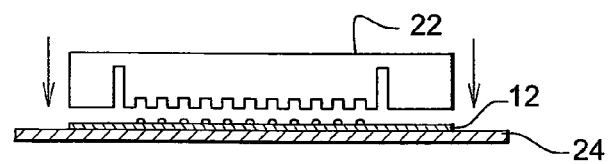
FIGS. 2, 3, and 4 are diagrams showing different steps in making a variant embodiment of the device.
Figure 3:
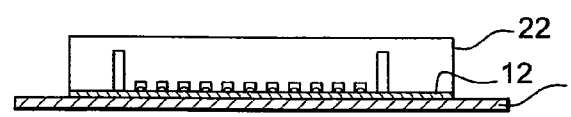

As shown in FIG. 2, the device 22 is then placed on a substrate 12 carried by a support 24, the top face of the substrate 12 carrying a set of probes 14 as described above with reference to FIG. 1.

When the polymer of the device 22 is only partially cured or polymerized during molding of the device, then a final curing or polymerization step is performed on the device in order to fasten it to the substrate.

In other circumstances, if the polymer of the device 22 does not adhere sufficiently to the substrate 12, a layer of optical adhesive is placed on the device 22 prior to placing it on the substrate 12, and it is irradiated with ultraviolet radiation once the device has been put into place on the substrate. In a variant, it is also possible to use a pressure-sensitive adhesive.

Figure 4:
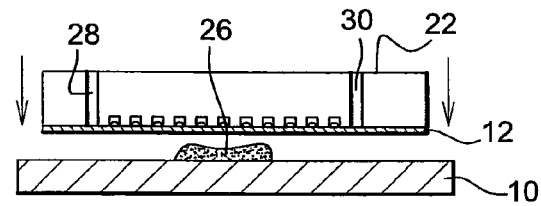
Figure 5:
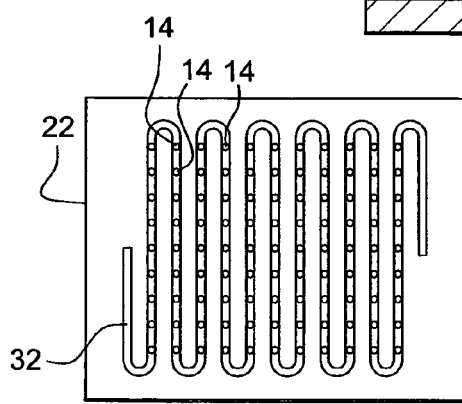
FIG. 5 is a diagrammatic plan view of the FIG. 4 device.

Thereafter, the assembly comprising the device 22 and the substrate 12 is separated from the support 24 and the assembly is placed on a sensor 10, as shown in FIG. 4, with at least partial index continuity optionally being ensured between the substrate and the sensor by means of a drop 26 of liquid or of a gel having an appropriate index that is placed on the sensor 10, possibly being associated with a block or wafer or optical fibers, as described above with reference to FIG. 1.

When the substrate 12 is made of flexible material, e.g. of PDMS, or when it has a bottom layer made of such a flexible material, it suffices to apply pressure to ensure optical contact between the substrate 12 and the sensor 10.

Figure 6:
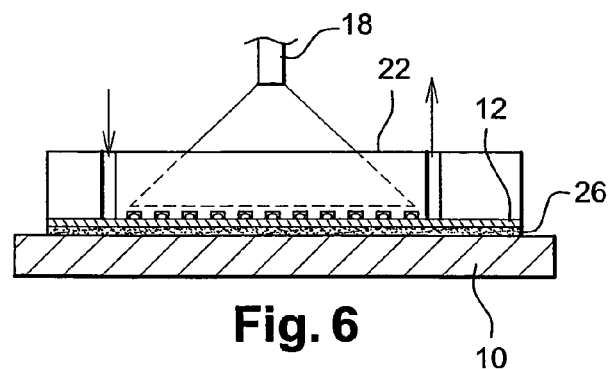
FIG. 6 shows the use of the device when placed on a sensor.

It is then necessary to feed the device 22 with fluid and to illuminate it with a suitable light source that emits at the excitation wavelength of the fluorescent markers and that is placed above the device 22, as shown diagrammatically in FIG. 6, so as to be able to track in real time the fixing of biological targets on the probes of the substrate.

As described with reference to FIG. 1, it is also necessary to place a stop filter for rejecting the excitation light between the probes 14 and the sensor 10, which filter may form a portion of the substrate or of the sensor or may be added thereto, as mentioned above.

In the embodiment shown in the drawing, the device 22 has a liquid feed duct 28 and a liquid outlet duct 30 passing through its entire thickness and communicating via their bottom ends with at least one channel 32 recessed in the bottom face of the device 22 and configured to pass via all of the probes 14 carried by the substrate 12 (FIG. 5), or with a set of channels that are connected to one another and that pass via the probes 14 of the substrate 12. It is necessary to align the channels 32 with the probes 14, but there is no need to align the channels on the sensor.

Figure 7:
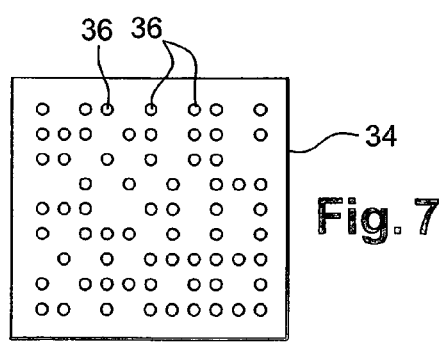
FIG. 7 is a diagram showing the image obtained by the sensor of the FIG. 6 device.
Figure 8:
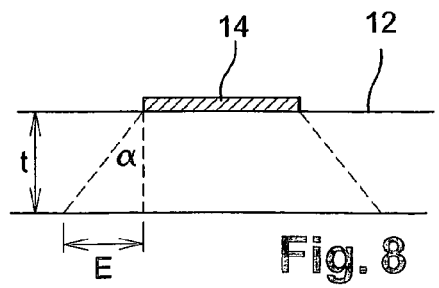
FIG. 8 is an enlarged diagrammatic view of the fuzzy halo that surrounds each spot in the image of FIG. 7.

The sensor serves to obtain an image of the substrate 12 such as the image 34 shown diagrammatically in FIG. 7, which image includes a certain number of light spots 36 corresponding to those probes 14 on which target molecules associated with fluorescent markers have become fixed. The light intensity of each spot 36 is a function of the number of target molecules that have become fixed on the probe 14 at that spot.

It is found that each light spot 36 presents a fuzzy halo, thereby making it necessary to use appropriate algorithms for processing the image by filtering or by segmentation. The extent E of the fuzzy halo around each light spot 36 is determined by the radiation pattern of the fluorescent markers or chromophores used. The shape of the halo also depends on the optical transfer function of the block or wafer of optical fibers. It is possible to use a block or wafer of fibers that presents spreading that is negligible, of the order of the distance between the pixels of the sensor.

For a chromophore placed at a glass/air interface, emission is concentrated in a cone of about 120° about the normal, with a main peak at about 40° from the normal. If t is the thickness of the substrate 12 and $\alpha$ is the emission angle, then the extent E of the fuzzy halo is given by $t.\tan\alpha$.

When the substrate 12 is a glass slide having thickness of 0.17 mm with air above it, the extent E of the halo is equal to 0.15 mm.

To limit this effect and to increase the effectiveness of light collection (i.e. the quantity of light that is transmitted into the substrate), it is desirable to use substrates having a refractive index that is as high as possible or a stack of dielectric layers of the Bragg mirror type, particularly when measurements are performed in a liquid phase, since the refractive index of the medium above the substrate 12 is then equal to about 1.3, instead of 1 for air.

The device of the invention may also be used when the phenomenon observed for detection purposes is luminescence. Under such circumstances, the targets are bonded to an enzyme substrate that emits photons when a reactive chemical species is added.

The invention claimed is:

1. A method of imaging and detecting the fluorescence emitted by chromophores fixed on a substrate, by illuminating the chromophores at an excitation wavelength and by picking up the light emitted by the chromophores in response to said illumination, said substrate being at least partially transparent at the emission wavelength of the chromophores and carrying biological probes configured to be put into contact with looked-for biological targets, the method being characterized in that it comprises placing or fastening a fluid flow device on the substrate, the fluid flow device having channels and/or chambers for introducing or circulating fluids, putting the substrate carrying the fluid flow device into contact with a sensor, while interposing a stop filter between the chromophores and the sensor to reject the excitation wavelength, the filter being transparent at the emission wavelength, using the fluid flow device to bring biological targets into contact with the probes fastened on the substrate, and illuminating the substrate at the excitation wavelength of the chromophores, and using the sensor to detect the light signals emitted by the chromophores.

2. A method according to claim 1, characterized in that at least partial index continuity is ensured between the substrate and the sensor.

3. A method according to claim 1, characterized in that an image of the probes is transmitted to the sensor by means of a block or wafer of optical fibers.

4. A method according to claim 1, characterized in that once the light signals emitted by the chromophores have been acquired, the sensor is separated from the substrate and is reusable with another substrate.

5. A device for imaging and detecting the fluorescence emitted by chromophores fixed on a substrate, by executing the method according to claim 1, the device comprising a substrate that is at least partially transparent at the emission wavelength of the chromophores and means for imaging, detecting and acquiring the light emitted by the chromophores in response to their light excitation, these means comprising a photo sensor characterized in that it comprises:

a fluid flow device including channels and/or chambers for introducing or circulating fluid, designed to be placed or fastened on the substrate to bring biological targets into contact with the probes fastened on the substrate and placed with the substrate onto the sensor, a stop filter that rejects the excitation wavelength of the chromophores, mounted between the chromophores and the sensor;

means for putting the substrate into optical contact with the sensor to form an image of the chromophores on the sensor, and enabling the substrate to be separated from the sensor after it has been used.

6. A device according to claim 5, characterized in that the substrate comprises a thin plate of glass or sapphire, a film of a plastics material, a polarizing filter, a set of optical fibers, or a set of capillary tubes containing the probes.

7. A device according to claim 6, characterized in that the substrate comprises a plastics material comprising polydimethylsiloxane.

8. A device according to claim 5, characterized in that the substrate is formed by the stop filter that rejects light at the excitation wavelength.

9. A device according to claim 5, characterized in that the stop filter comprises an absorbent filter, or a reflective filter, or a combination of absorbent and reflective filters.

10. A device according to claim 5, characterized in that it includes means providing index continuity between the substrate and the sensor, said means comprising a thin layer of liquid or gel or flexible material of suitable index connecting the substrate to the sensor.

11. A device according to claim 5, characterized in that the fluid flow device is made of glass by etching or of polymer by molding, thermoforming, or assembling polymer films that include cutouts corresponding to the above-mentioned channels and/or chambers.

12. A device according to claim 5, wherein the photo sensor comprises a matrix of CCD or CMOS type photodetectors or a photosensitive emulsion.

13. A method according to claim 1, wherein the sensor comprises a matrix of CCD or CMOS type photodetectors or a photosensitive emulsion.

* * * * *